(12) United States Patent
Sliwa et al.

(10) Patent No.: US 10,512,754 B2
(45) Date of Patent: Dec. 24, 2019

(54) SENSOR-BEARING TIP AND MEDICAL DEVICE INCLUDING THE SAME

(71) Applicant: St. Jude Medical, Cardiology Division, Inc., St. Paul, MN (US)

(72) Inventors: John W. Sliwa, San Jose, CA (US); Zhenyi Ma, Santa Clara, CA (US); Stephen A. Morse, Menlo Park, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 575 days.

(21) Appl. No.: 15/101,545

(22) PCT Filed: Dec. 19, 2014

(86) PCT No.: PCT/US2014/071434
§ 371 (c)(1),
(2) Date: Jun. 3, 2016

(87) PCT Pub. No.: WO2015/108666
PCT Pub. Date: Jul. 23, 2015

(65) Prior Publication Data
US 2016/0303345 A1    Oct. 20, 2016

Related U.S. Application Data

(60) Provisional application No. 61/927,289, filed on Jan. 14, 2014.

(51) Int. Cl.
*A61B 8/14* (2006.01)
*A61M 25/00* (2006.01)
(Continued)

(52) U.S. Cl.
CPC ....... *A61M 25/007* (2013.01); *A61B 1/00096* (2013.01); *A61B 1/00177* (2013.01);
(Continued)

(58) Field of Classification Search
None
See application file for complete search history.

(56) References Cited

U.S. PATENT DOCUMENTS

| | | | |
|---|---|---|---|
| 4,901,735 A | 2/1990 | von Berg | |
| 5,484,433 A * | 1/1996 | Taylor | A61B 18/245 606/10 |

(Continued)

FOREIGN PATENT DOCUMENTS

| | | |
|---|---|---|
| EP | 1080684 | 3/2001 |
| WO | 1990/008502 | 8/1990 |
| WO | 2014/152575 | 9/2014 |

*Primary Examiner* — Joel F Brutus
(74) *Attorney, Agent, or Firm* — Wiley Rein LLP

(57) ABSTRACT

A tip for a medical device includes a hollow body having a window, a sensor positioned within the hollow body and oriented such that its active surface is pointed towards the window, and a membrane positioned within a beam path of the sensor. The membrane passes energy without preventing an outer surface of the hollow body of the tip from coming in contact with tissue, thus allowing the hollow body to deliver therapy to an adjacent tissue and/or diagnose adjacent tissue. The membrane can cover the window or the sensor. The membrane is desirably permeable to an irrigant, such that a suitable level of irrigant outflow from the window is maintained, and thin enough that it minimizes attenuation of energy passing to and/or from the sensor.

22 Claims, 5 Drawing Sheets

(51) Int. Cl.
*A61B 8/12* (2006.01)
*A61B 1/00* (2006.01)
*A61B 1/015* (2006.01)
*A61B 5/00* (2006.01)
*A61B 18/14* (2006.01)
*A61B 8/00* (2006.01)
*A61B 18/00* (2006.01)
*A61B 17/00* (2006.01)
*A61B 90/00* (2016.01)

(52) U.S. Cl.
CPC ............ *A61B 1/015* (2013.01); *A61B 5/0084* (2013.01); *A61B 5/4836* (2013.01); *A61B 5/4848* (2013.01); *A61B 5/6853* (2013.01); *A61B 8/12* (2013.01); *A61B 8/445* (2013.01); *A61B 18/1492* (2013.01); *A61B 2017/00106* (2013.01); *A61B 2018/00029* (2013.01); *A61B 2018/00285* (2013.01); *A61B 2018/00577* (2013.01); *A61B 2090/065* (2016.02); *A61B 2217/007* (2013.01); *A61B 2218/002* (2013.01); *A61B 2560/0443* (2013.01); *A61B 2562/16* (2013.01)

(56) References Cited

U.S. PATENT DOCUMENTS

| | | | |
|---|---|---|---|
| 5,904,147 A * | 5/1999 | Conlan | A61M 25/0108 128/899 |
| 5,967,990 A | 10/1999 | Thierman et al. | |
| 2002/0087156 A1* | 7/2002 | Maguire | A61B 18/00 606/41 |
| 2005/0054905 A1 | 3/2005 | Corl et al. | |
| 2005/0107738 A1* | 5/2005 | Slater | A61M 25/10 604/96.01 |
| 2007/0167813 A1* | 7/2007 | Lee | A61B 8/12 600/459 |
| 2010/0168624 A1* | 7/2010 | Sliwa | A61B 6/12 601/3 |
| 2010/0326843 A1 | 12/2010 | Zhang | |
| 2011/0009857 A1* | 1/2011 | Subramaniam | A61B 18/1492 606/33 |
| 2011/0257523 A1* | 10/2011 | Hastings | A61B 8/0891 600/439 |
| 2012/0265069 A1 | 10/2012 | Sliwa et al. | |
| 2013/0090650 A1* | 4/2013 | Jenson | A61B 18/1492 606/41 |

* cited by examiner

SENSOR-BEARING TIP AND MEDICAL DEVICE INCLUDING THE SAME

CROSS-REFERENCE TO RELATED APPLICATIONS

This application claims the benefit of U.S. provisional application No. 61/927,289, filed 14 Jan. 2014, which is hereby incorporated by reference as though fully set forth herein.

BACKGROUND

The instant disclosure relates to medical devices. In particular, the instant disclosure relates to sensor-bearing tips that can be mounted to medical devices for use in the human body, such as diagnostic and therapeutic catheters.

Catheters are used in a variety of diagnostic and therapeutic procedures, for example to diagnose and/or treat conditions such as atrial arrhythmias. For example, a catheter carrying one or more electrodes can be deployed and manipulated through a patient's vasculature and, once located at the intended site, radiofrequency ("RF") energy can be delivered through the electrodes to ablate tissue. Alternatively, or in addition, the electrodes can be used to create a map of the electrophysiological activity of the patient's heart. Further, the electrodes can be used to localize (that is, determine the position and orientation of) the catheter as it is deployed and manipulated to the intended site.

In some catheters, an additional sensor, such as an ultrasound sensor or optical sensor, is provided in the catheter tip to provide additional information during performance of the primary diagnosis or therapy. For example, RF ablation catheters can include one or more ultrasound sensors, located within the hollow tip of the catheter, that can be used to monitor the progress of a lesion forming in the tissue being treated and/or to confirm one or more characteristics of the lesion once created.

Extant sensor-bearing tip medical devices, however, are subject to various issues, including excessive irrigant outflow, the passage of debris from the interior of the medical device into the patient's body, and distortion of signals to and/or from the sensors. Although there are known solutions to some of these problems, they very often exacerbate others (e.g., a rigid cover can be used to prevent the passage of debris, but increases signal distortion).

BRIEF SUMMARY

Disclosed herein is a tip for a medical device that includes: a hollow body including a window; a sensor including an active surface positioned within the hollow body and oriented such that the active surface is pointed towards the window; and a membrane positioned within a beam path of the sensor, wherein the membrane passes energy without preventing an outer surface of the hollow body of the tip from coming in contact with tissue. The membrane can be positioned such that it covers the window, for example by securing it to either an outer surface of the hollow body or an inner surface of the hollow body. The membrane can also have its outer edge proximate the perimeter of the window. Alternatively, the membrane can take the form of a balloon secured within the hollow tip.

In other aspects, the membrane can be positioned such that it covers the sensor. For example, the membrane can be adjacent to the sensor or adhered to the sensor, such as by chemically vapor depositing the membrane material onto the sensor.

In some embodiments, the sensor is an acoustic sensor and the membrane is an acoustically-transmissive membrane.

The sensor can sense energy coming from tissue and, in some embodiments, can transmit energy to the tissue and sense returning and/or reflected energy. The energy emitted by the sensor can be a different form of energy than the energy used by the tip to provide diagnosis and/or therapy. For example, the sensor can emit ultrasonic energy, and the tip can use radiofrequency energy to provide ablation therapy.

In some embodiments, the membrane is permeable to an irrigant. This can be accomplished, for example, by using a hydrophilic material for the membrane, by treating the membrane to be hydrophilic, by using a porous (e.g., microor macro-porous) material for the membrane, and/or by forming irrigation holes in the membrane (e.g., by laser drilling).

Typically, the membrane will be flexible. It can also exhibit elastomeric, viscoelastomeric, or plastic properties when deformed.

Certain advantages can be achieved by making the membrane thin, including the minimization of acoustic distortion and the attenuation of energy passing through the membrane (e.g., passing to and/or from the sensor). Thus, for example, the membrane can have a thickness of no more than 30 microns, such as between 5 microns and 25 microns or between 10 microns and 20 microns.

Also disclosed herein is a medical device including: an elongate tubular body having a distal section and including a lumen extending along its length; a hollow tip, including a window, attached to the distal end of the elongate tubular body, wherein the lumen of the elongate tubular body is in fluid communication with an interior of the hollow tip; a sensor disposed within the hollow body, wherein the sensor comprises an active surface oriented towards the window; and a membrane positioned between the active surface of the sensor and the window. The membrane can be secured to the hollow tip or, alternatively, to the elongate tubular body.

In another aspect, a tip for a medical device includes: a hollow body including a window; a sensor including an active surface positioned within the hollow body and oriented such that the active surface is pointed towards the window; a membrane deposited upon and overlying the sensor; and an irrigant dam positioned to restrict outflow of irrigant from the window. The membrane can include a chemically vapor deposited poly(p-xylylene), such as Parylene™.

The foregoing and other aspects, features, details, utilities, and advantages of the present invention will be apparent from reading the following description and claims, and from reviewing the accompanying drawings.

DETAILED DESCRIPTION

The present disclosure provides sensor-bearing tips for use in medical devices and medical devices including the same. The tips can have a diagnostic or therapeutic function, with the sensor(s) used to monitor such function. For purposes of illustration, several exemplary embodiments will be described in detail herein in the context of a radiofrequency ("RF") ablation catheter including an acoustic sensor (e.g., a pulse-echo transducer) that can be used to monitor the progress of the lesion being formed in an adjacent tissue. It should be understood, however, that the methods, apparatuses, and systems described herein can be utilized in other contexts (e.g., optical sensors).

Figure 1:
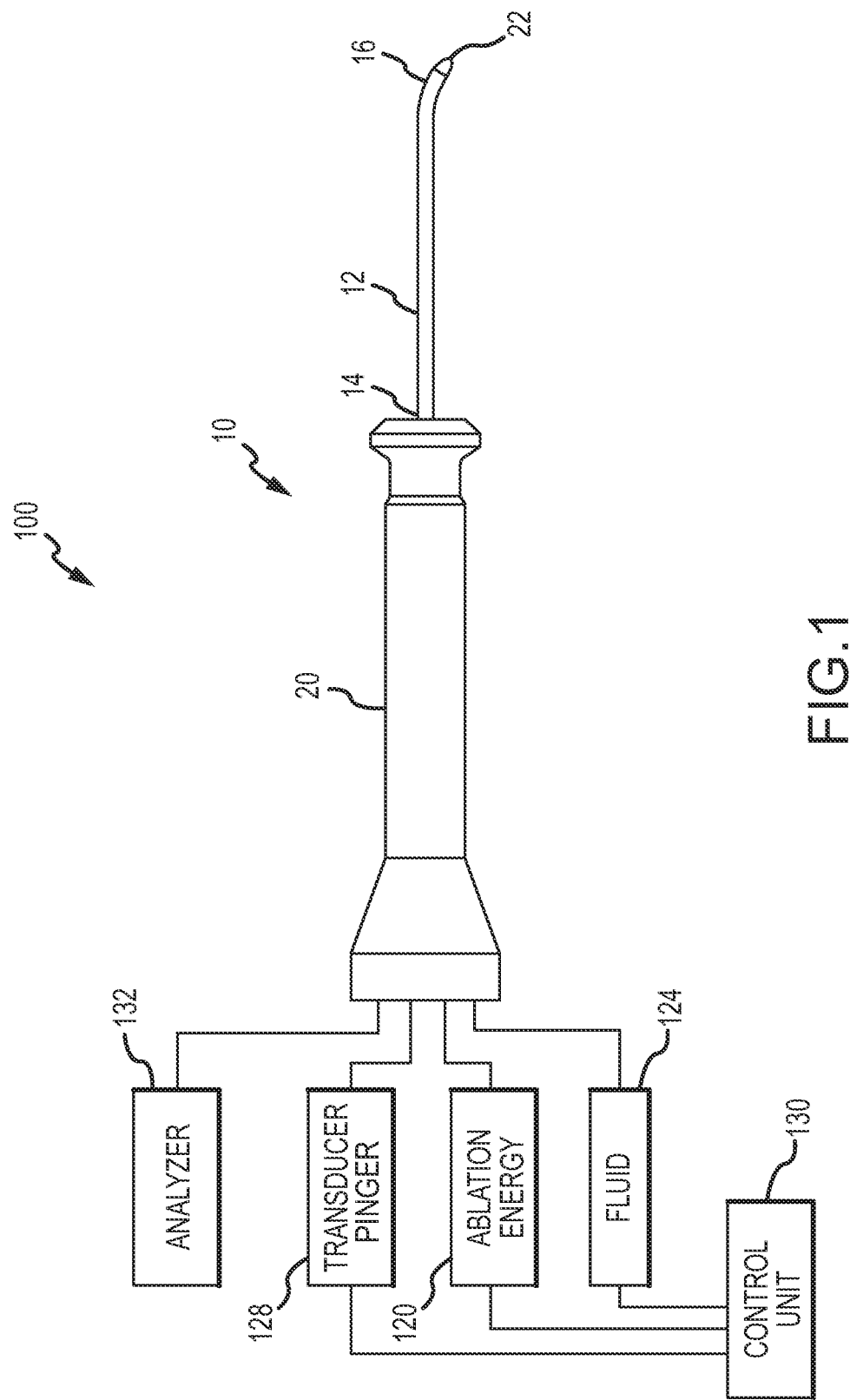
FIG. 1 depicts an exemplary catheter including a sensor-bearing hollow tip.

FIG. 1 is a schematic diagram of an ablation system 100 including an exemplary catheter 10. As shown in FIG. 1, catheter 10 generally includes an elongate tubular body 12 having a proximal end 14 and a distal end 16. Tubular body 12 defines a lumen 18 (not visible in FIG. 1, but shown in FIGS. 2-7). Although only a single lumen 18 is depicted in the figures, this is only for the sake of clarity of illustration; tubular body 12 can have any number of lumens 18 without departing from the scope of the instant teachings.

Proximal end 14 of tubular body 12 is attached to a catheter control handle 20. Catheter control handle 20 can include, for example, an actuator (not shown) coupled to suitable structure (e.g., pull wires and/or pull rings) within tubular body 12 in order to effect the deflection of distal end 16. It can also include connections to additional components of ablation system 100 as discussed in further detail below. Insofar as the construction of catheter control handle 20 will be familiar to those of ordinary skill in the art and a detailed understanding thereof is not necessary to make and use the teachings herein, however, no further description need be provided.

A hollow tip 22 is attached to distal end 16 of tubular body 12. Tip 22 can be a diagnostic tip, a therapeutic tip, a hybrid diagnostic and therapeutic tip, or any other type of tip that may be desirable for a given application of catheter 10.

For example, tip 22 can include an RF ablation element, such as a tip electrode. As such, catheter 10 can be connected with an ablation energy source 120, such as an RF generator.

Figure 2:
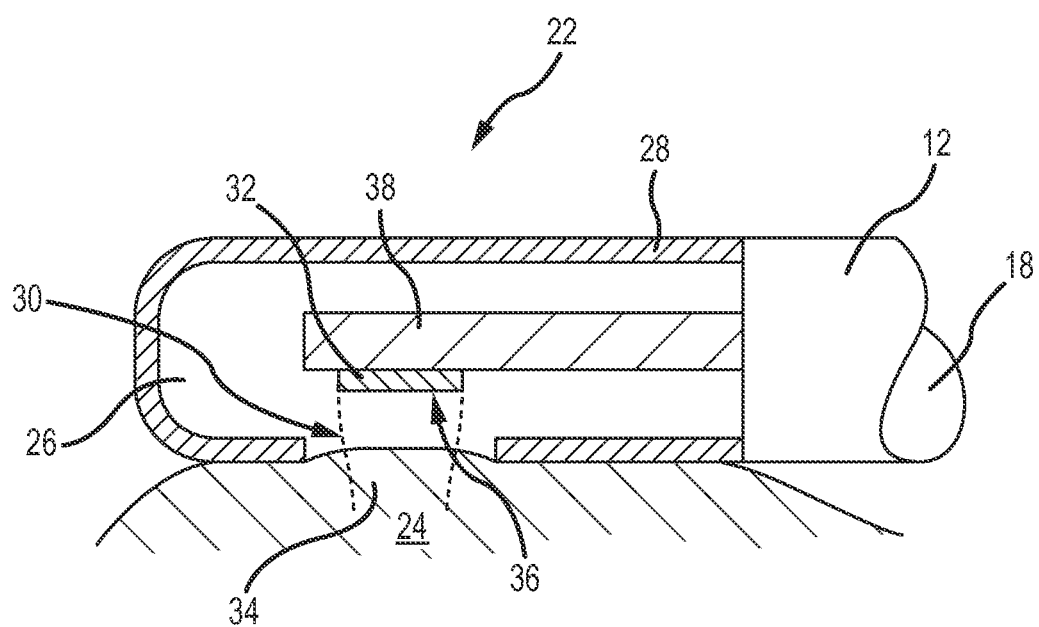
FIG. 2 illustrates an exemplary sensor-bearing hollow tip mounted to a catheter body in close up and partial cut-away view.

FIG. 2 is a close-up and partial cross-section of hollow tip 22 (and a portion of tubular body 12 proximate distal end 16) against a tissue surface 24. As shown in FIG. 2, lumen 18 of tubular body 12 is in fluid communication with the interior 26 of hollow tip 22, which is defined by a wall 28 of hollow tip 22. An irrigant (e.g., saline) or other fluid can be delivered from fluid source 124 (shown in FIG. 1), through lumen 18, and into hollow tip 22, for example for cooling purposes, for energy transmission purposes, and/or for acoustic matching purposes.

Wall 28 of hollow tip 22 further includes a window or ("beam hole") 30 (e.g., a break in wall 28). Window 30 allows for the passage of energy to and/or from a sensor 32, which, in some embodiments, is an ultrasound transducer, disposed within interior 26 of hollow tip 22 along a beam path 34. It is therefore desirable for window 30 to be larger than the active surface 36 of sensor 32, which is oriented towards window 30, to minimize or eliminate diffraction and/or attenuation of energy passing to and/or from sensor 32 by reducing the likelihood that incoming and/or outgoing energy will pass through or otherwise impinge the edges of wall 28 defining window 30.

As illustrated, sensor 32 is mounted to an acoustic backer 38, but any suitable structure to secure sensor 32 within hollow tip 22 can be employed. Backer 38 can be acoustically attenuative, such that any acoustic energy that propagates backwards from sensor 32 towards backer 38, rather than towards tissue 24, is attenuated. This also allows acoustic sensor 32 to have a short acoustic ring-down time, making it suitable for the transmission of short pulses for pulse-echo lesion sensing.

Window 30 also allows for irrigant to pass out of interior 26 of hollow tip 22, for example for tissue cooling purposes, energy transmission purposes, and/or for energy coupling to adjacent tissue. The irrigant, such as saline, can benefit the coupling and transmission of both RF ablation energy and pulse-echo acoustic energy to (and, in the case of pulse-echo energy, from) tissue 24. Tissue 24 may naturally distend into window 30.

A transducer pinger 128 (see FIG. 1), which might have more than one channel, supplies pinging energy, such as electrical energy pulses, to sensor 32 (e.g., an ultrasound transducer). A control unit 130 (also shown in FIG. 1) is provided for controlling the ablation and the acoustic pinging during ablation. For instance, control unit 130 can be configured to carry out duty cycling or synchronization for both ablation and pinging. An acoustic pinger echo analyzer or acoustic receiver 132 is provided to condition and analyze the data collected by sensor 32 to provide one or more of lesion feedback, tissue thickness or proximity measurement, tip contact force monitoring, and pre-pop detection. The information can be presented to a practitioner (e.g., using a graphical user interface) to provide real-time assessment of the ablation. The information may additionally or alternatively be utilized by the system itself without operator intervention, for example as input to a feedback control loop to avoid steam pops and/or to achieve a desired lesion depth.

Thus, one aspect disclosed herein is directed to an RF ablation catheter with one or more acoustic transducers therein or thereon, wherein the acoustic transducer is capable of at least one of acoustic lesion feedback, catheter tip-force monitoring, tissue thickness or proximity measurement, or pre-pop warning. The catheter is capable of delivering an RF ablating tip to a patient's tissue to be ablated. These aspects and others are described in U.S. patent application publication no. 2012/0265069, which is hereby incorporated by reference as though fully set forth herein.

A fully-open window 30, however, has certain attendant disadvantages. For example, it allows for a very substantial volume of irrigant outflow, which can starve smaller irrigation passageways (e.g., apertures that are not also intended to pass energy to and/or from a sensor) of irrigant. This results in decreased irrigant backpressure in hollow tip 22, which can in turn lead to increased bubble formation due to a reduced boiling point, particularly when the temperature of hollow tip 22 increases during use (e.g., where hollow tip 22 functions as a radiofrequency ("RF") ablation electrode).

Similarly, a fully-open window 30 presents no obstacles to the passage of potentially harmful debris into the patient's body if, for example, a portion of sensor 32 were to break off.

Though extant devices mitigate some of these concerns (e.g., a rigid polymeric acoustic covering over window 30 reduces the risk of debris passing into the patient's body), they do so at the expense of other desirable aspects (e.g., a rigid polymeric acoustic covering over window 30 can defocus and attenuate ultrasonic energy passing therethrough and/or limit the outflow of irrigant to such an extent that blood coagulates at window 30 or the tissue becomes dewetted). The embodiments disclosed herein advantageously allow the simultaneous achievement of multiple desirable attributes—including, without limitation, an appropriate volume of irrigant outflow, the prevention of debris escape, avoidance of beam distortion, and the minimization of window-edge diffraction and/or attenuation of energy passing to and/or from sensor 32—by placing a membrane within beam path 34 of sensor 32 (that is, between active surface 36 of sensor 32 and tissue 24).

Figure 3:
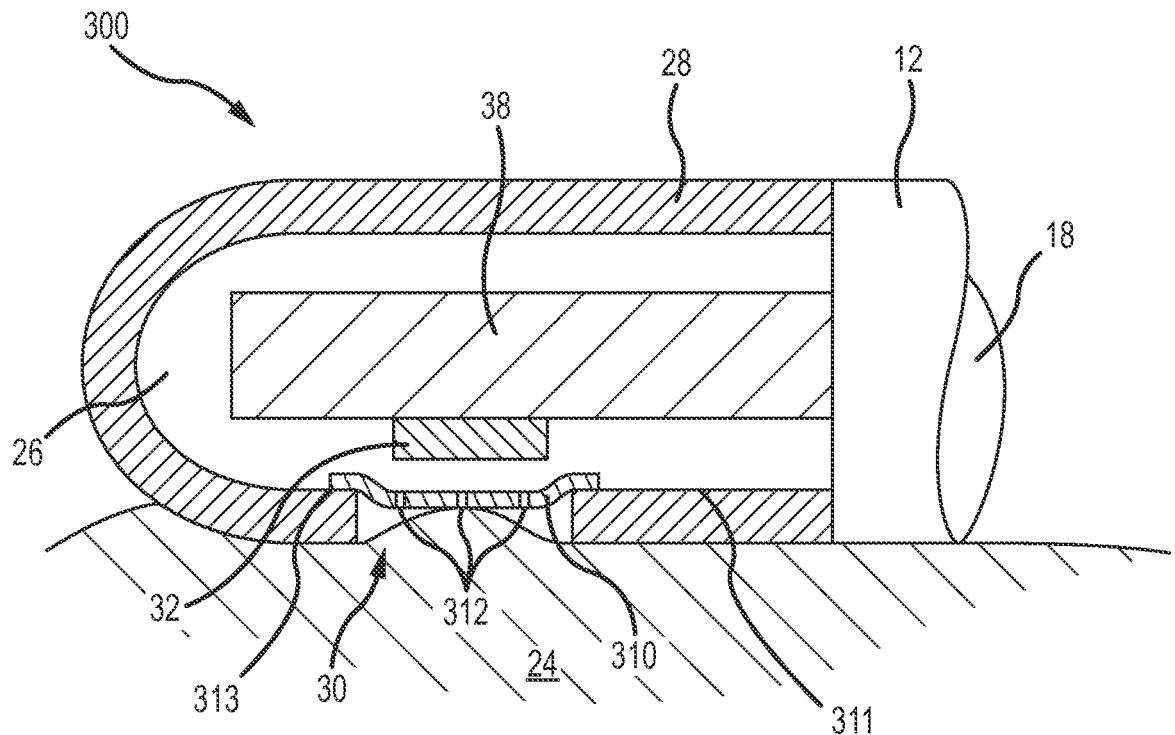
FIG. 3 illustrates a first embodiment of a sensor-bearing hollow tip as disclosed herein mounted to a catheter body in close up and partial cut-away view.

A first embodiment of a sensor-bearing hollow tip 300 is depicted in FIG. 3. As shown in FIG. 3, a membrane 310 covers window 30. In particular, membrane 310 is secured to the inner surface 311 of wall 28, for example by thermoforming an outer periphery 313 of membrane 310 to wall 28 under heat and pressure or by securing the outer periphery 313 of membrane 310 to wall 28 with a suitable adhesive. Outer periphery 313 of membrane 310 is proximate the perimeter of window 30; that is, membrane 310 is roughly the same size and shape (e.g., round, oval, or other shape) as window 30.

Figure 4:
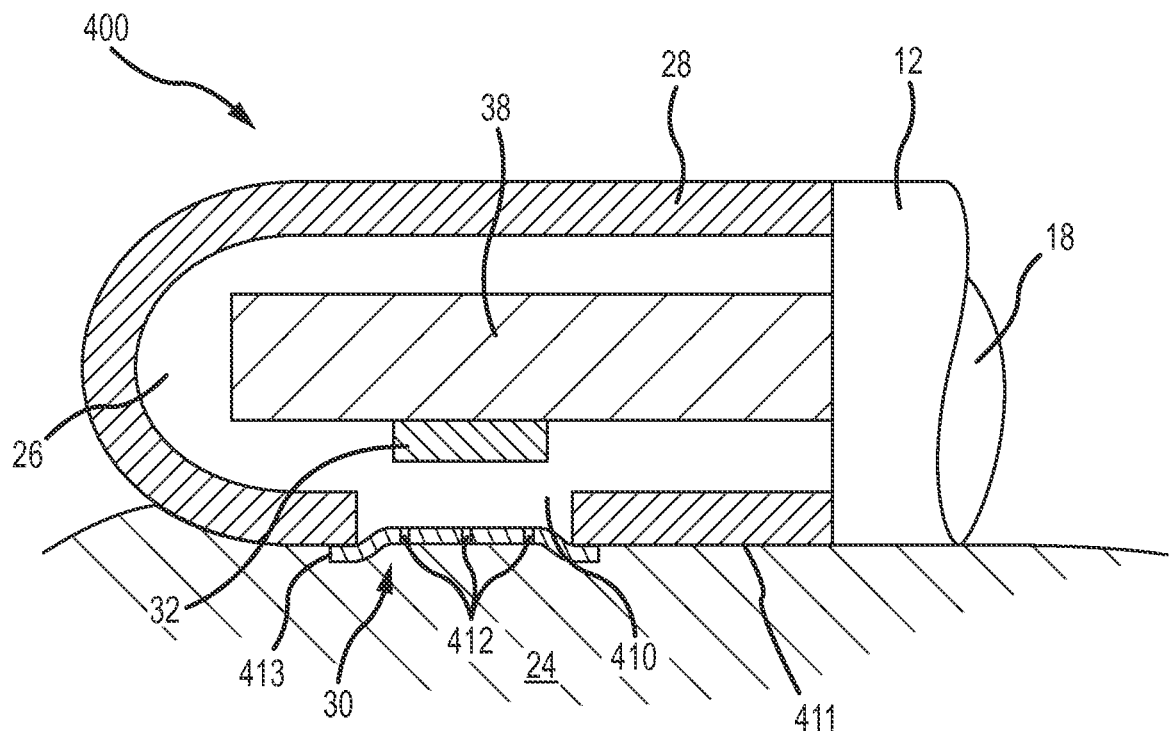
FIG. 4 illustrates a second embodiment of a sensor-bearing hollow tip as disclosed herein mounted to a catheter body in close up and partial cut-away view.

A second embodiment of a sensor-bearing hollow tip 400 is depicted in FIG. 4. The embodiment of FIG. 4 is similar to that of FIG. 3, except that membrane 410 is secured to the outer surface 411 of wall 28, for example by thermoforming an outer periphery 413 of membrane 410 to wall 28 under heat and pressure or by securing outer periphery 413 of membrane 410 to wall 28 with a suitable adhesive. Outer periphery 413 of membrane 412 is proximate the perimeter of window 30; that is, membrane 410 is roughly the same size and shape as window 30.

Figure 5:
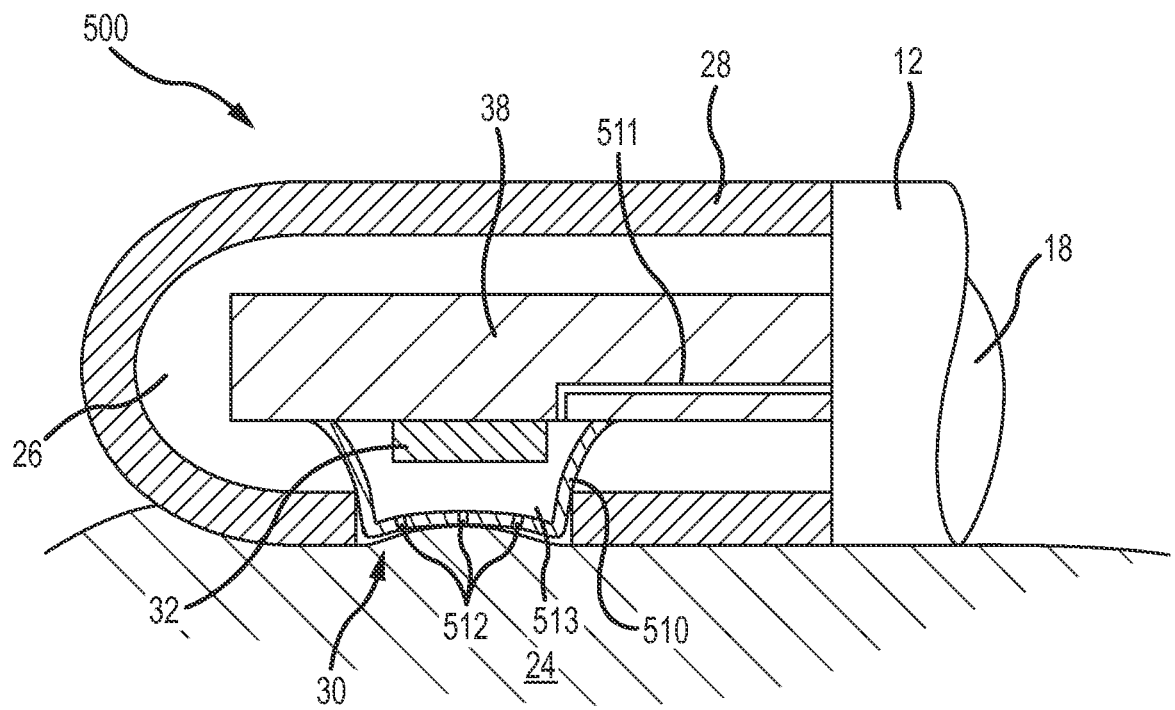
FIG. 5 illustrates a third embodiment of a sensor-bearing hollow tip as disclosed herein mounted to a catheter body in close up and partial cut-away view.

A third embodiment of a sensor-bearing hollow tip 500 is depicted in FIG. 5. As shown in FIG. 5, a membrane 510 is secured proximate sensor 32, for example to acoustic backer 38. To inflate membrane 510, there is an inlet (e.g., passageway 511) to deliver irrigant (or another suitable inflation fluid) to the space 513 between membrane 510 and sensor 32/acoustic backer 38).

Figure 6:
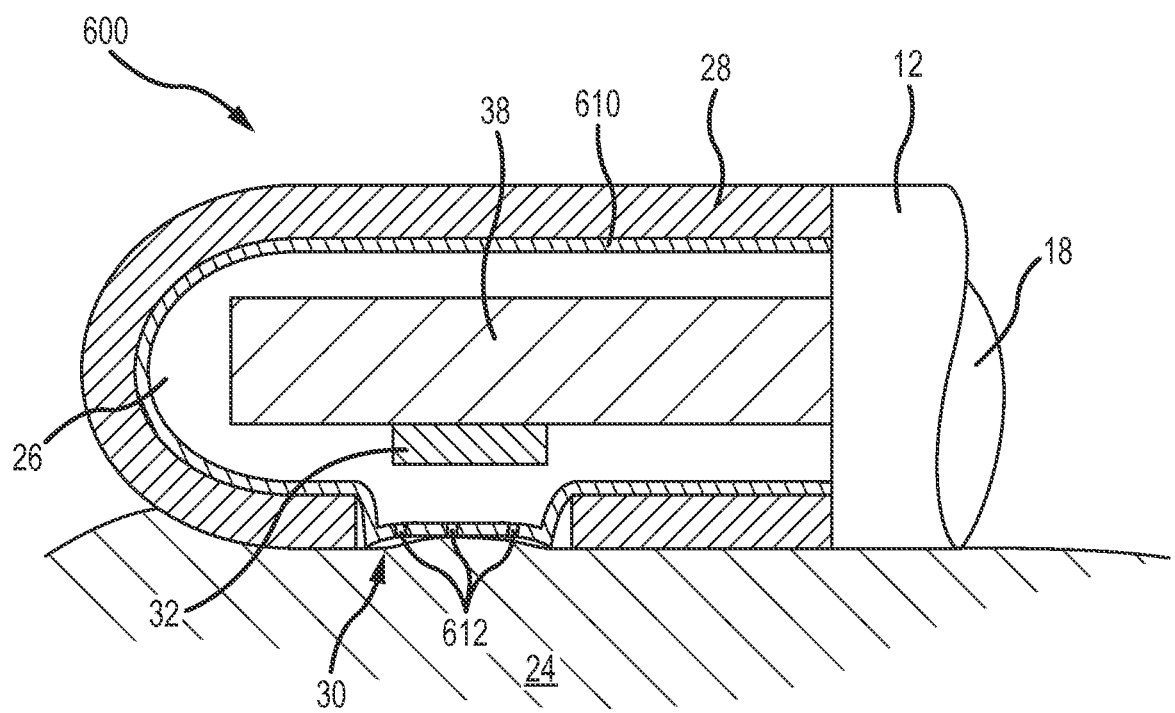
FIG. 6 illustrates a fourth embodiment of a sensor-bearing hollow tip as disclosed herein mounted to a catheter body in close up and partial cut-away view.

FIG. 6 depicts another embodiment of a hollow tip 600. In the embodiment of FIG. 6, membrane 610 comprises a balloon (or bladder) that is inflated against the inner surface of wall 28, for example under pressure of an irrigant or other suitable inflation fluid, when in use. Membrane 610 can be secured to elongate tubular body 12, for example by thermoforming membrane 610 to elongate tubular body 12 under heat and pressure at one or more locations interior to hollow tip 600.

It is desirable for membranes 310, 410, 510, 610 to be wettable by irrigant (e.g., saline), for example by using a material that is either naturally hydrophilic to the irrigant or has been treated to be hydrophilic to the irrigant.

It is also desirable for membranes 310, 410, 510, 610 to be permeable to the irrigant (that is, membranes 310, 410, 510, 610 should permit the irrigant to pass through its thickness). For example, a microporous, micropermeable, or foamlike material can be used for membrane 310, 410, 510, 610. Alternatively or additionally, a plurality of irrigation holes 312, 412, 512, 612 can be provided in membranes 310, 410, 510, 610 respectively, for example by laser-drilling or punching. Because irrigant flow out of windows 30 will be limited, however, by the presence of permeable membranes 310, 410, 510, 610 there remains net positive irrigant pressure inside hollow tip 300, 400, 500, 600, which in turn suppresses bubble formation, boil-over, and thrombus formation.

Where sensor 32 is an acoustic sensor, membranes 310, 410, 510, 610 can be acoustically-transmissive. Suitable materials for membranes 310, 410, 510, 610 include, without limitation, polyether ether ketone ("PEEK") (e.g., the APTIV™ films of Victrex), polyethylene terephthalate ("PET"), polyvinyl chloride ("PVC"), nylon, urethane, polyethylene, latex, and silicone.

Membranes 310, 410, 510, 610 are flexible, in order to attain a curvilinear shape in window 30, for example under pressure of an irrigant. In addition to being flexible, membranes 310, 410, 510, 610 can be elastomeric (e.g., deforming elastically under irrigant pressure), viscoelastomeric (e.g., deforming elastically under irrigant pressure, but returning to its relaxed state after a time delay), plastic (e.g., deforming plastically under irrigant pressure), or may exhibit a combination of the foregoing properties.

According to certain aspects, membranes 310, 410, 510, 610 have a thickness of no more than about 30 microns. For example, membranes 310, 410, 510, 610 can each have a thickness between about 5 microns and about 25 microns, or between about 10 microns and about 20 microns. At these dimensions, acoustic distortion and attenuation of energy passing to and/or from sensor 32 are minimized, but the membrane itself remains able to withstand the irrigant pressure.

The embodiments discussed above offer the advantages of simultaneously allowing a desirable volume of irrigant outflow, preventing debris escape, avoiding beam distortion, providing excellent acoustic coupling to wetted tissue, and minimizing diffraction and attenuation of energy passing to and/or from sensor 32. Each embodiment also offers additional advantages beyond those discussed above. For example, in hollow tips 300 and 600, the bond between membrane 310, 610 and wall 28 or elongate tubular body 12 is protected from abrasion against tissue 24 when catheter 10 is in use.

As another exemplary advantage of the embodiment illustrated in FIG. 3, because membrane 310 is only slightly larger than window 30, there is less interference with the ability of an irrigant delivered to hollow tip 300 to cool the interior of wall 28 before flowing out of hollow tip 300 (e.g., through irrigant holes 312 or additional irrigation passageways (not shown) in wall 28).

Hollow tips 400, 500, and 600 offer the additional exemplary advantage of easier installation of membrane 410, 510, 610 resulting from the ability to see the point(s) at which the membrane is bonded during assembly. That is, unlike membrane 310, membranes 410, 510, and 610 are not attached to wall 28 at a blind point.

Figure 7:
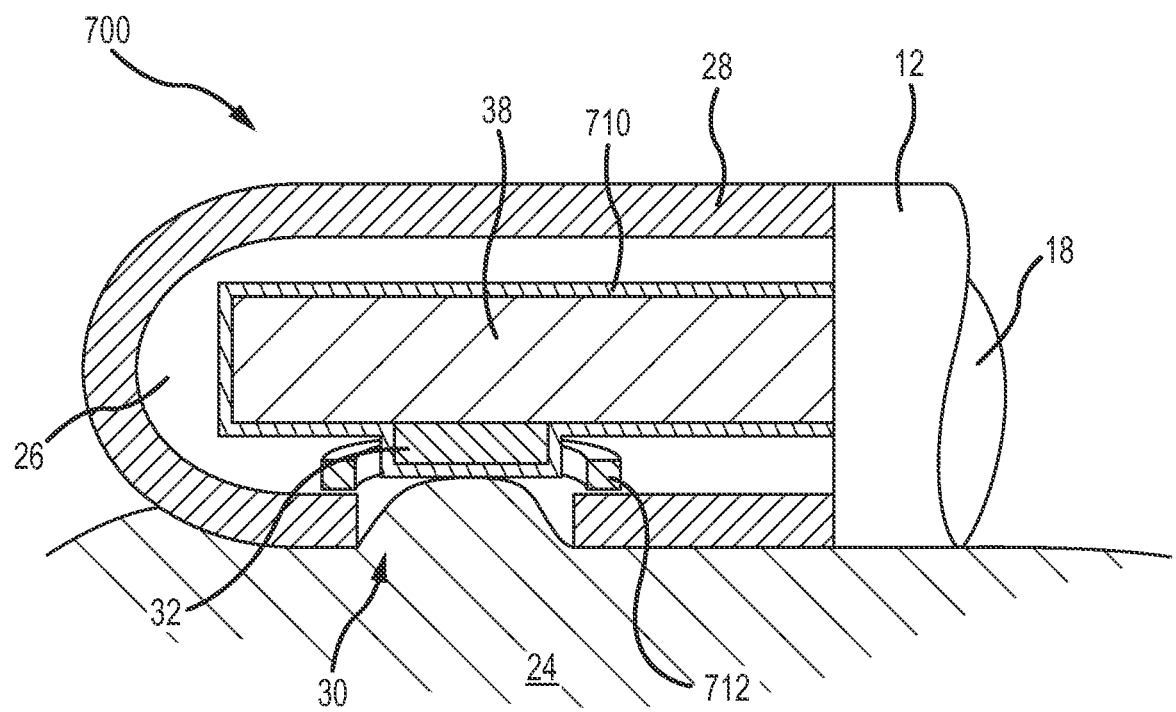
FIG. 7 illustrates a fifth embodiment of a sensor-bearing hollow tip as disclosed herein mounted to a catheter body in close up and partial cut-away view.
Figure 8:
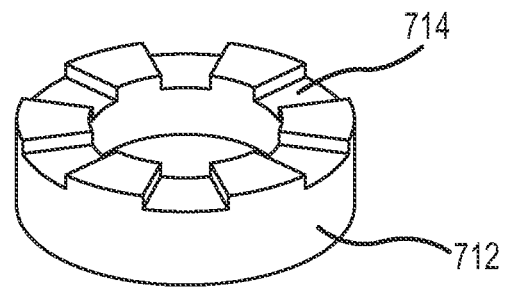
FIG. 8 is a close up view of the ring-shaped dam shown in FIG. 7.

Still another embodiment of hollow tip 700 is shown in FIG. 7. As shown in FIG. 7, a membrane 710 is placed closely around sensor 32 and acoustic backer 38. Indeed, membrane 710 can be directly deposited upon sensor 32 and acoustic backer 38. Membrane 710 can be used in conjunction with a ring-shaped dam 712, formed, for example, of a compressible rubber or foam material, at or near window 30 to control the flow of irrigant out of hollow tip 700. As shown in FIG. 8, ring-shaped dam 712 can include a plurality of flow passageways 714 designed to promote a suitable volume of irrigant outflow from window 30.

Membrane 710 can be a chemically vapor-deposited layer of a poly-para-xylylene, such as Parylene™, and, in particular, Parylene™ C. Such materials are desirably pin-hole free and can be precisely deposited over irregular surfaces substantially conformally. Membrane 710 can have a thickness of between about 10 microns and 15 microns.

Additional exemplary advantages (e.g., beyond the prevention of debris escape and the other advantages discussed above) of membrane 710 include increased mechanical capture of sensor 32 in the event of breakage, increased high voltage leakage protection, and ease of assembly.

In addition, membrane 710 does not distend towards tissue under irrigant pressure. Instead, membrane 710 remains bonded to sensor 32 and acoustic backer 38.

Although several embodiments of this invention have been described above with a certain degree of particularity, those skilled in the art could make numerous alterations to the disclosed embodiments without departing from the spirit or scope of this invention.

For example, although the exemplary embodiments are discussed and illustrated in connection with a single sensor, the teachings herein are equally applicable to devices including additional sensors and/or more than a single window. Indeed, certain aspects disclosed herein are particularly advantageous in medical devices including several sensors (e.g., three radially-looking sensors arranged circumferentially about the hollow tip at about 120° intervals and a fourth forward-looking sensor).

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A tip for a medical device, the tip comprising:
a hollow body including a window, wherein the hollow body comprises a radiofrequency electrode;
a sensor including an active surface positioned within the hollow body and oriented such that the active surface is pointed towards the window; and
a membrane positioned within a beam path of the sensor, wherein the membrane is configured to pass energy without preventing an outer surface of the radiofrequency electrode from coming in contact with tissue.

2. The tip according to claim 1, wherein the membrane covers the window.

3. The tip according to claim 2, wherein the membrane is secured to an outer surface of the hollow body.

4. The tip according to claim 2, wherein the membrane is secured to an inner surface of the hollow body.

5. The tip according to claim 4, wherein the membrane comprises a balloon or bladder secured within the hollow tip.

6. The tip according to claim 2, wherein an outer edge of the membrane is proximate a perimeter of the window.

7. The tip according to claim 1, wherein the membrane covers the sensor.

8. The tip according to claim 7, wherein the membrane is adjacent the sensor.

9. The tip according to claim 1, wherein the sensor comprises an acoustic sensor and wherein the membrane comprises an acoustically-transmissive membrane.

10. The tip according to claim 1, wherein the membrane is permeable to an irrigant.

11. The tip according to claim 10, wherein the membrane is treated to be hydrophilic to the irrigant.

12. The tip according to claim 10, wherein the membrane comprises a plurality of irrigation holes.

13. The tip according to claim 1, wherein the membrane comprises an elastomeric material.

14. The tip according to claim 1, wherein the membrane has a thickness of no more than 30 microns.

15. The tip according to claim 1, wherein:
the hollow body comprises a plurality of windows;
the sensor comprises a plurality of sensors, each having an active surface oriented towards a respective one of the plurality of windows; and
the membrane comprises at least one membrane positioned within the beam path of each of the plurality of sensors.

16. The tip according to claim 15, wherein the at least one membrane comprises a single membrane positioned within the beam path of all of the plurality of sensors.

17. A medical device, comprising:
an elongate tubular body having a distal end and including a lumen extending along its length;
a hollow tip, including a window, attached to the distal end of the elongate tubular body, wherein the lumen of the elongate tubular body is in fluid communication with an interior of the hollow tip, and wherein the hollow tip comprises a radiofrequency electrode;
a sensor disposed within the hollow body, wherein the sensor comprises an active surface oriented towards the window; and
a membrane positioned between the active surface of the sensor and the window, wherein the membrane is configured to pass energy without preventing an outer surface of the radiofrequency electrode from coming in contact with tissue.

18. The medical device according to claim 17, wherein the membrane is secured to the hollow tip.

19. The medical device according to claim 17, wherein the membrane is secured to the elongate tubular body.

20. A tip for a medical device, the tip comprising:
a hollow body including a window, wherein the hollow body comprises a radiofrequency electrode;
a sensor including an active surface positioned within the hollow body and oriented such that the active surface is pointed towards the window;
a membrane deposited upon and overlying the sensor, wherein the membrane is configured to pass energy without preventing an outer surface of the radiofrequency electrode from coming in contact with tissue; and
an irrigant dam positioned to restrict outflow of irrigant from the window.

21. The tip according to claim 20, wherein the membrane comprises a chemically vapor deposited poly(p-xylylene).

22. The tip according to claim 20, wherein the irrigant dam comprises a ring including a plurality of flow passageways.

* * * * *